United States Patent
Marchosky

(10) Patent No.: US 6,835,208 B2
(45) Date of Patent: Dec. 28, 2004

(54) PROSTHETIC SYSTEM

(76) Inventor: J. Alexander Marchosky, 224 S. Woods Mill Rd., Chesterfield, MO (US) 63017

( * ) Notice: Subject to any disclaimer, the term of this patent is extended or adjusted under 35 U.S.C. 154(b) by 0 days.

(21) Appl. No.: 10/151,500

(22) Filed: May 20, 2002

(65) Prior Publication Data

US 2002/0138145 A1 Sep. 26, 2002

Related U.S. Application Data

(63) Continuation of application No. 09/377,283, filed on Mar. 30, 1999, now Pat. No. 6,413,278.
(60) Provisional application No. 60/135,095, filed on Mar. 30, 1998, now abandoned.

(51) Int. Cl.$^7$ .................................................. A61F 2/44
(52) U.S. Cl. ................................. 623/17.16; 623/17.11
(58) Field of Search ........................... 623/17.11, 17.13, 623/17.15, 17.16; 606/61

(56) References Cited

U.S. PATENT DOCUMENTS

| | | |
|---|---|---|
| 2,677,369 A | 5/1954 | Knowles |
| 4,265,618 A | 5/1981 | Herskovitz et al. |
| 4,349,921 A | 9/1982 | Kuntz |

(List continued on next page.)

FOREIGN PATENT DOCUMENTS

CA 2229714 * 5/1997

OTHER PUBLICATIONS

D. Adams and D.F. Williams "Carbon Fiber–Reinforced Carbon as a Potential Implant Material", *Journal of Biomedical Materials Research* 12 (1978): 35–42.

G. Jenkins and F. De Carvalho "Biomedical Applications of Carbon Fibre Reinforced Carbon in Implanted Protheses", *Carbon* 15 (1977): 33–37.
J. Parsons, et al. "Long–Term Follow–Up of Achilles Tendon Repair with an Absorable Polymer Carbon Fiber Composite", *Foot & Ankle* vol. 9, No. 4 Feb. 1989): 179–84.
J. Thebault, et al. "Biomechanical and Biological Aspects of Carbon Composites (SEPCARB® and CERASEP®)", *Progress in Science and Engineering of Composites ICC–M–IV (1982)*: 1185–93.
D. Resnick, et al. "Biomechanics of the Thoracolumbar Spine", *Neurosurgery Clinics of North America* vol. 8, No. 4 (Oct. 1997): 455–69.
P. Ciapetta, et al. "A Carbon Fiber Reinforced Polymer Cage for Vertebral Body Replacement", *Neurosurgery* vol. 41, No. 5 (Nov. 1997): 1203–06.
C. Ray "Threaded Titanium Cages for Lumbar Interbody Fusions", *Spine* vol. 22, No. 6 (1997): 667–80.
C. Ray "Threaded Fusion Cages for Lumbar Interbody Fusions: an Economic Comparison with 360° Fusions", *Spine* vol. 22, No. 6 (1997): 681–85.
J. Brantigan, et al. "A Carbon Fiber Implant to Aid Interbody Lumbar Fusion: Mechanical Testing", *Spine* vol. 16, No. 6 Supplement (1991): S277–82.

*Primary Examiner*—Bruce E Snow
(74) *Attorney, Agent, or Firm*—Sonnenschein Nath & Rosenthal LLP

(57) ABSTRACT

A spinal prosthesis for insertion during surgery in a space between first and second vertebrae of a spine includes a central support sized and shaped for insertion between the first and second vertebrae. The support has a height measured between a top and a bottom approximately equal to a selected spacing between the first and second vertebrae. Upper and lower flex members extend from the top and bottom of the central support, respectively, for engaging the first and second vertebrae. The upper and lower members have a stiffness sufficiently small to permit the members to flex elastically toward each other under loading from the first and second vertebrae.

22 Claims, 17 Drawing Sheets

U.S. PATENT DOCUMENTS

| | | |
|---|---|---|
| 4,704,088 A | 11/1987 | Newman |
| 4,743,256 A | 5/1988 | Brantigan |
| 4,834,757 A | 5/1989 | Brantigan |
| 4,878,915 A | 11/1989 | Brantigan |
| 4,892,545 A | 1/1990 | Day et al. |
| 4,997,432 A | 3/1991 | Keller |
| 5,011,484 A | 4/1991 | Bréard |
| 5,147,402 A | 9/1992 | Bohler et al. |
| 5,192,327 A | 3/1993 | Brantigan |
| 5,306,310 A | 4/1994 | Siebels |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,522,899 A | 6/1996 | Michelson |
| 5,562,738 A | 10/1996 | Boyd et al. |
| 5,571,189 A | 11/1996 | Kuslich |
| 5,607,424 A | 3/1997 | Tropiano |
| 5,658,337 A | 8/1997 | Kohrs et al. |
| 5,676,702 A | 10/1997 | Ratron |
| 5,749,916 A * | 5/1998 | Richelsoph .................. 623/17 |
| 5,904,719 A | 5/1999 | Errico et al. |
| 6,146,420 A * | 11/2000 | McKay .................... 623/17.16 |
| 6,224,631 B1 | 5/2001 | Kohrs |
| 6,371,988 B1 * | 4/2002 | Pafford et al. ........... 623/17.11 |
| 6,413,278 B1 * | 7/2002 | Marchosky ............... 623/17.11 |
| 6,482,233 B1 * | 11/2002 | Aebi et al. ............... 623/17.11 |

\* cited by examiner

FIG. 9
FIG. 10
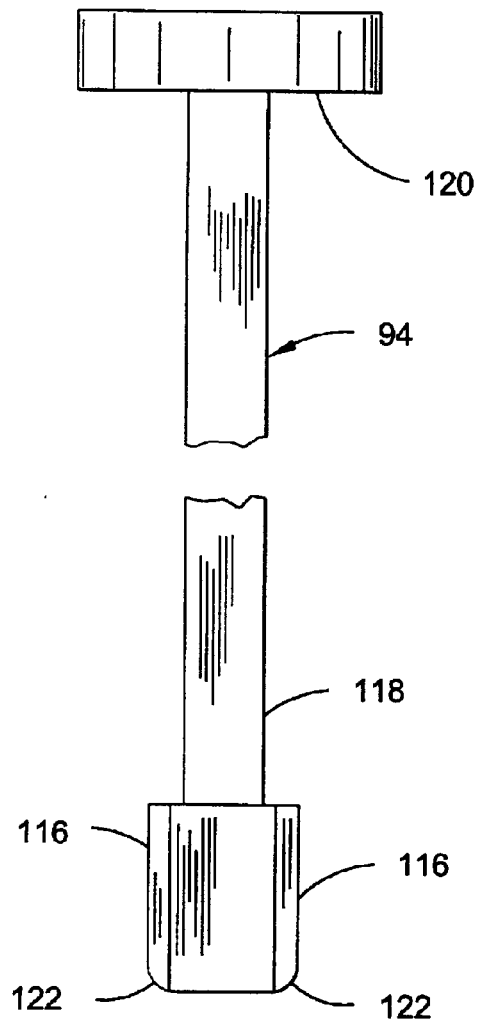
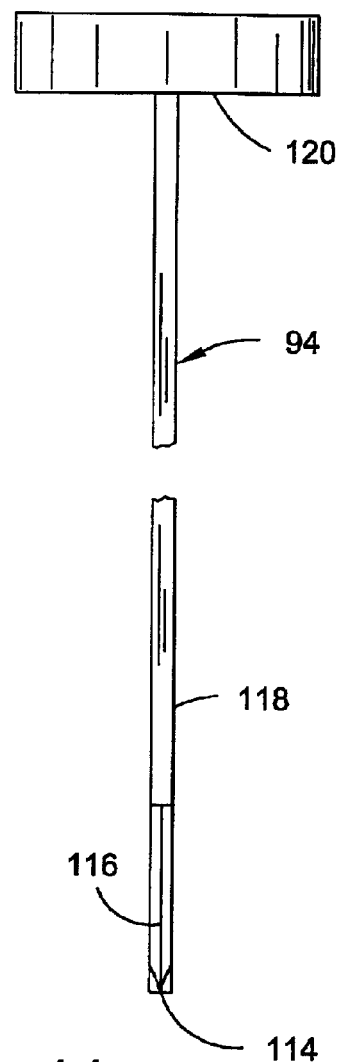
FIG. 11
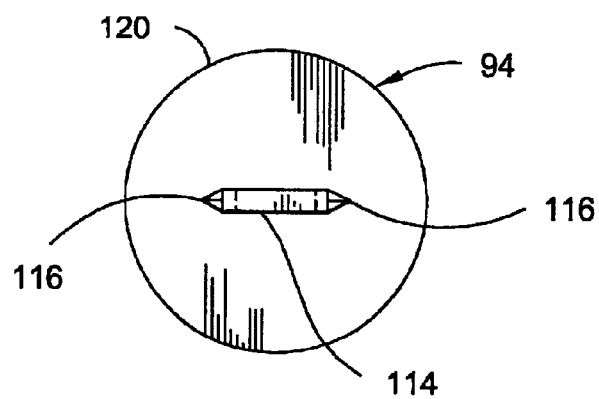

PROSTHETIC SYSTEM

CROSS-REFERENCE TO RELATED APPLICATION

This application is a continuation of application Ser. No. 09/377,283, filed Mar. 30, 1999 now U.S. Pat. No. 6,413,278 which is a complete application based on provisional application Ser. No. 60/135,095 which was converted from nonprovisional application Ser. No. 09/050,498, filed Mar. 30, 1998 now abandoned, and incorporated herein by reference for all purposes.

BACKGROUND OF THE INVENTION

The present invention relates generally to a prosthetic system, and more particularly to mechanical and biological spinal prostheses, as well as a method and apparatus for inserting the prostheses between vertebrae of a spine.

Degenerative disease of the spine, which is caused by stresses imposed on the spine by trauma and normal loading, as well as genetics and other factors, results in abnormal motion between vertebrae beyond normal limits. Eventually, if uncorrected, the degenerative processes can lead to pain, deformity, musculoskeletal dysfunction and neurologic dysfunction. When other measures fail to alleviate these symptoms, surgical intervention is required.

Typically, the surgical intervention involves implanting mechanical and/or biological prostheses between affected vertebrae of the spine to immobilize the affected vertebrae and eventually fuse them together. Mechanical prostheses restore anatomical curvature to the spine, prevent deformity from progressing and immobilize the vertebrae to promote fusion of the vertebrae. Biological prostheses are sometimes used, alone or in combination with mechanical prostheses, to promote bone growth between the vertebrae, thereby facilitating fusion of the vertebrae. The biological prostheses are generally made of bone harvested from the patient or some other donor.

According to a principle known as Wolff's Law, bone growth is stimulated and directed by loading the bone which occurs naturally as a person moves. For instance, growth of bone through biological prostheses may be stimulated by loading the prostheses. However, conventional mechanical prostheses are relatively rigid and do not permit the biological prostheses to be loaded in a natural manner due to "stress shielding". As a result, bone growth is not stimulated when biological prostheses and conventional mechanical prostheses are used in combination. Accordingly, the efficacy of the prosthetic system is reduced when biological and conventional mechanical prostheses are used together.

Biological prostheses conduct and direct bone growth from exposed recipient bone. When biological prostheses are implanted between vertebrae, bone grows inward from the facing surfaces of the vertebrae adjacent the biological prosthesis, eventually growing together and fusing the vertebrae. As will be appreciated by those skilled in the art, the speed at which the bone grows and the overall success of the prosthetic system is greatly affected by the surface area of the vertebrae exposed to the biological prosthesis. However, many prior art mechanical prostheses contact the adjacent vertebrae over large areas and prevent the biological prostheses from contacting the vertebral surfaces. Thus, bone growth is inhibited, thereby reducing the efficacy of the prosthetic system.

Further, many conventional biological prostheses are composed only of fragments of bone. One desirable aspect of these "dry" prostheses is that they stay in position between vertebrae. However, it is sometimes desirable to add liquid to the prostheses. For instance, liquid growth factors are added to the biological prostheses for stimulating bone growth. However, the liquid additives make the prostheses highly flowable. As a result, available biological protheses containing growth factors frequently flow out from position between the vertebrae, thereby reducing their efficacy.

In addition, conventional mechanical prostheses and the conventional tools used to implant them have relatively wide profiles, requiring large portions of the discs or surrounding structures and tissues such as pedicles, facets and ligaments to be removed before the prosthesis can be inserted. However, experience has shown that the more material removed from around the vertebrae, the more the trauma and the greater the chance for instability and failure of the surgery. Further, the wide profiles of conventional prostheses and tools increase the likelihood of permanent injury to the spinal cord and nerve roots, especially when the prostheses are inserted in the upper spine.

SUMMARY OF THE INVENTION

Among the several objects of the present invention may be noted the provision of a method and apparatus which correct and relieve pain associated with segmental instability of the spine; the provision of such a method and apparatus which limit the motion of adjacent vertebrae of a spine; the provision of such a method and apparatus which facilitate fusion of adjacent vertebrae; the provision of such a method and apparatus which promote bone and blood vessel growth between adjacent vertebrae; the provision of such a method and apparatus which minimize the risk of injury to the surrounding vertebrae and structures; and the provision of such a method and apparatus which permit introduction of a fluid biological prosthesis having sufficient viscosity to remain in position between vertebrae.

Briefly, the present invention includes a surgical method of inserting a prosthetic system between first and second vertebrae spaced by a disc to limit motion between and to facilitate fusion of the first and second vertebrae. The method comprises the steps of exposing the first and second vertebrae and the disc, excising at least a portion of the disc from between the first and second vertebrae, and scraping the cartilage from facing surfaces of the vertebrae to expose the facing surfaces. The method also includes the steps of spacing the first and second vertebrae by a selected distance and simultaneously cutting grooves in the facing surfaces of the vertebrae using a cutting tool having opposing blades. A mechanical prosthesis is anchored in the grooves cut in the facing surfaces of the vertebrae so that the prosthesis extends between the vertebrae and limits motion between the vertebrae. In addition, the method includes the step of packing bone graft material between the vertebrae and around the mechanical prosthesis to promote bone growth between and facilitate fusion of the vertebrae.

In another aspect, the present invention includes a spinal prosthesis for insertion during surgery in a space between first and second vertebrae of a spine of a patient. The prosthesis comprises a central support sized and shaped for insertion between the first and second vertebrae. The support has a height measured between a top and a bottom approximately equal to a selected spacing between the vertebrae. The prosthesis also includes upper and lower flex members extending from the top and bottom of the central support, respectively, for engaging the first and second vertebrae. The upper and lower members have a stiffness sufficiently small to permit the members to flex elastically toward each other under loading from the vertebrae.

In yet another aspect, the invention includes a spinal prosthesis comprising a central support, as well as upper and lower anchors positioned at the top and bottom of the support, respectively, for anchoring the support between the first and second vertebrae. Each anchor includes a sharp edge for holding the anchor in position with respect to the respective vertebra.

In still another aspect, the present invention includes a spinal prosthesis comprising a central support and at least one stiffener extending from the support for strengthening the support to inhibit flexing thereof.

In addition, the present invention includes a set of surgical instruments for inserting a prosthetic system between first and second vertebrae to limit motion between and/or to facilitate fusion of the vertebrae. The set of instruments comprises a spacer for positioning the first and second vertebrae in a selected orientation and spacing the vertebrae by a selected distance. The spacer has a tapered tip for facilitating insertion of the spacer between the vertebrae and opposing surfaces for engaging facing surfaces of the vertebrae thereby to position and space them. The set of instruments also includes a cutting tool having opposing blades for cutting grooves simultaneously in the facing surfaces of the first and second vertebrae and a guard adapted for attachment to the spacer. The guard has a passage sized for receiving the cutting tool to guide the tool between the facing surfaces of the vertebrae and to prevent the blades from errantly cutting structures surrounding the vertebrae.

Still further, the present invention includes a syringe for injecting bone graft material between first and second vertebrae to promote fusion of the vertebrae. The syringe comprises a body having a hollow interior and a nozzle communicating with the interior for delivering bone graft material from the hollow interior to a space between the vertebrae. In addition, the syringe includes a piston reciprocally receivable within the hollow interior of the cylindrical body for forcing bone graft material from the hollow interior through the nozzle. The piston and body have interengaging screw threads which drive the piston toward the nozzle to force bone graft material through the nozzle upon rotation of the threads relative to each other.

Moreover, the present invention includes a syringe for injecting bone graft material comprising a cylindrical body and a piston reciprocally receivable within a hollow interior of the cylindrical body for forcing bone graft material from the hollow interior through a nozzle. In addition, the syringe includes a heating element in thermal communication with the hollow interior of the cylindrical body for heating the bone graft material to a predetermined temperature.

Further, the present invention includes a syringe for injecting bone graft material comprising a cylindrical body having a hollow interior and a nozzle communicating with the interior for delivering bone graft material from the hollow interior to a space between the vertebrae. The syringe also includes a piston reciprocally receivable within the hollow interior of the cylindrical body for forcing bone graft material from the hollow interior into the nozzle. The piston has a hole extending through the piston aligned with the nozzle. In addition, the syringe comprises a plunger reciprocally received within the hole extending through the piston for forcing bone graft material through the nozzle.

The present invention also includes a fluid bone graft material for insertion during surgery in a space between first and second vertebrae of a spine of a patient to facilitate fusion of the first and second vertebrae. The material comprises a plurality of bone particles and a growth factor for stimulating bone growth. The material is sufficiently viscous to remain in place between the first and second vertebrae under loading by the vertebrae.

Other objects and features of the present invention will be in part apparent and in part pointed out hereinafter.

BRIEF DESCRIPTION OF THE DRAWINGS

FIG. 9 is a front elevation of a cutting tool of the present invention;

FIG. 10 is a side elevation of the cutting tool;

FIG. 11 is a bottom plan of the cutting tool;

Corresponding reference characters indicate corresponding parts throughout the several views of the drawings.

DETAILED DESCRIPTION OF THE PREFERRED EMBODIMENT

Figure 1:
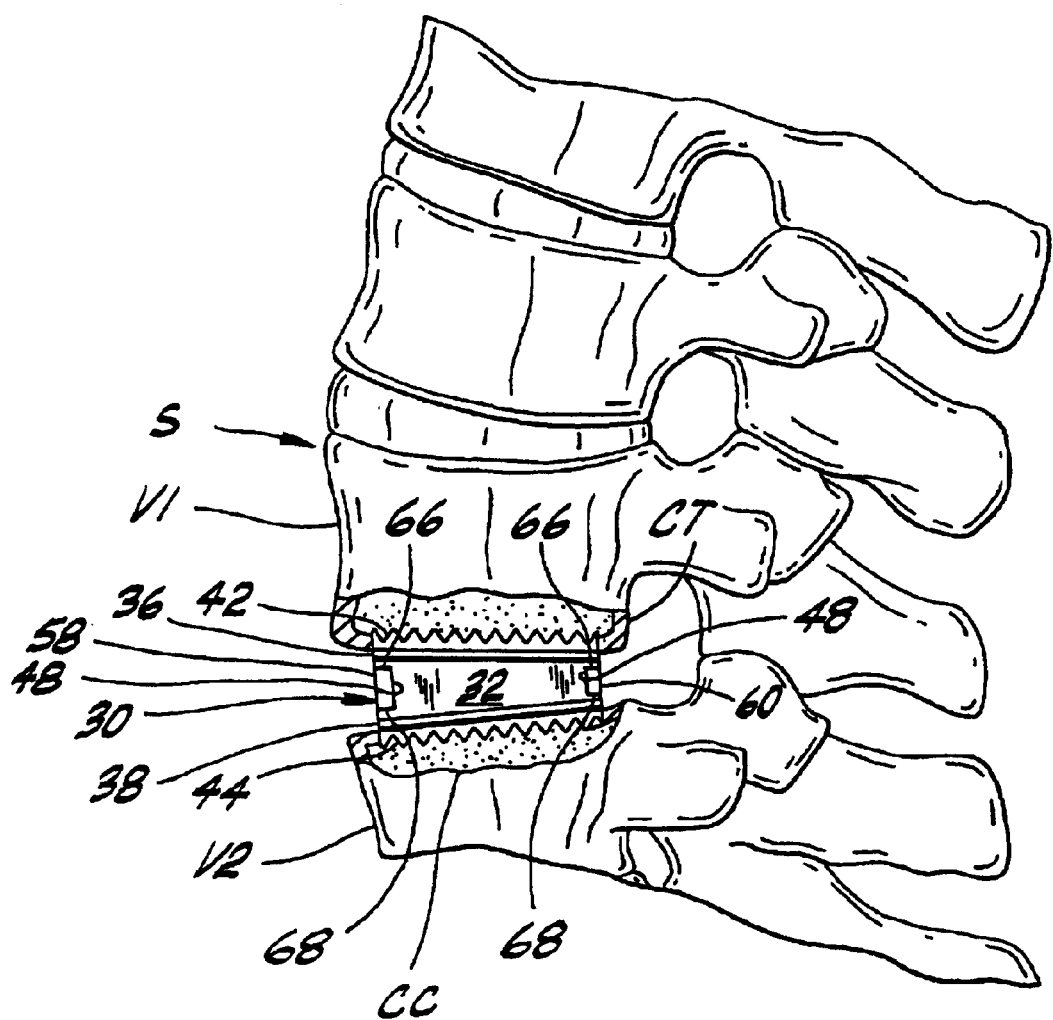
FIG. 1 is a side elevation of a mechanical prosthesis of the present invention in a space between first and second vertebrae shown in partial section for clarity.

Referring now to the drawings and in particular to FIGS. 1–4, a mechanical prosthesis is indicated in its entirety by the reference numeral 30. The prosthesis 30 generally comprises a central support 32, upper and lower flex members 36, 38 (respectively), upper and lower anchors 42, 44 (respectively) and stiffeners 48. As will be explained in greater detail below, the prosthesis is adapted for insertion between a first vertebra V1 and a second vertebra V2 of a spine, generally designated S.

The central support 32 is preferably a quadrilateral panel having a length greater than its height, opposite first and second faces 32a, 32b and a thickness significantly less than its height. Preferably, the support 32 has a height measured between its top and bottom approximately equal to a selected spacing between the first and second vertebrae V1, V2. Usually, the selected spacing refers to a spacing slightly larger than the most desirable spacing practicably obtainable between the vertebrae so that the most desirable spacing practicably obtainable is achieved between the vertebrae after the vertebrae are seated on the anchors 42, 44 of the prosthesis 30 as will be explained below. However, other spacings may also be used without departing from the scope of the present invention. As illustrated in FIG. 1, the front end of the support (to the left as shown) is taller than its back end, so that when the prosthesis 30 is inserted, the first vertebra V1 is angled relative to the second vertebra V2. As will be explained in more detail below, the front and back ends of the support may have equal heights without departing from the scope of the present invention. The support 32 is thin to reduce the volume of the prosthesis 30 and to present a narrow profile yet provide enough strength to support the spine S. It is contemplated that the lateral faces of the support may be grooved, knurled or otherwise patterned to improve gripping when the prosthesis 30 is installed.

The prosthesis 30 may be constructed of numerous different biocompatible materials. It may be a metallic, non-metallic or composite material, but the preferred construction is a carbon fiber-reinforced polymer composite. It is also envisioned that the polymer may include other carbon-based organic molecules (a biomolecular substrate) for enhancing bone and blood vessel growth (osteogenesis, osteoconduction and angiogenesis) through and/or around the prosthesis. Additionally, mineral salts may be added to the substrate to enhance stability and incorporation of the material. Although materials having other characteristics may be used without departing form the scope of the present invention, in the preferred embodiment the strength of the material in compression, torsion and shear and the modulus of elasticity closely approximate the strength and elasticity of the cortical bone CT forming the outer layer of the vertebrae V1, V2. In the case of carbon fiber-reinforced materials, this can be accomplished by weaving the fibers in a multidirectional pattern, as will be understood by those skilled in the art. Preferably, the material is radiolucent to allow healing to be monitored and imaged without distortion using standard radiographic techniques. Most preferably, the reinforcing material and/or the substrate material of the prosthesis is absorbable by the patient so that the stiffness of the prosthesis 30 decreases over time after it is inserted in the spine S. Although other materials may be used without departing from the scope of the present invention, the material of the preferred embodiment is a carbon fiber reinforced carbon composite material such as Integraft polymer coated carbon fiber available from Hexcel Medical of Livermore, Calif. Both of these preferred materials are radiolucent and absorbable, however other materials which are non-radiolucent and/or non-absorbable are also within the scope of the present invention.

Figure 3:
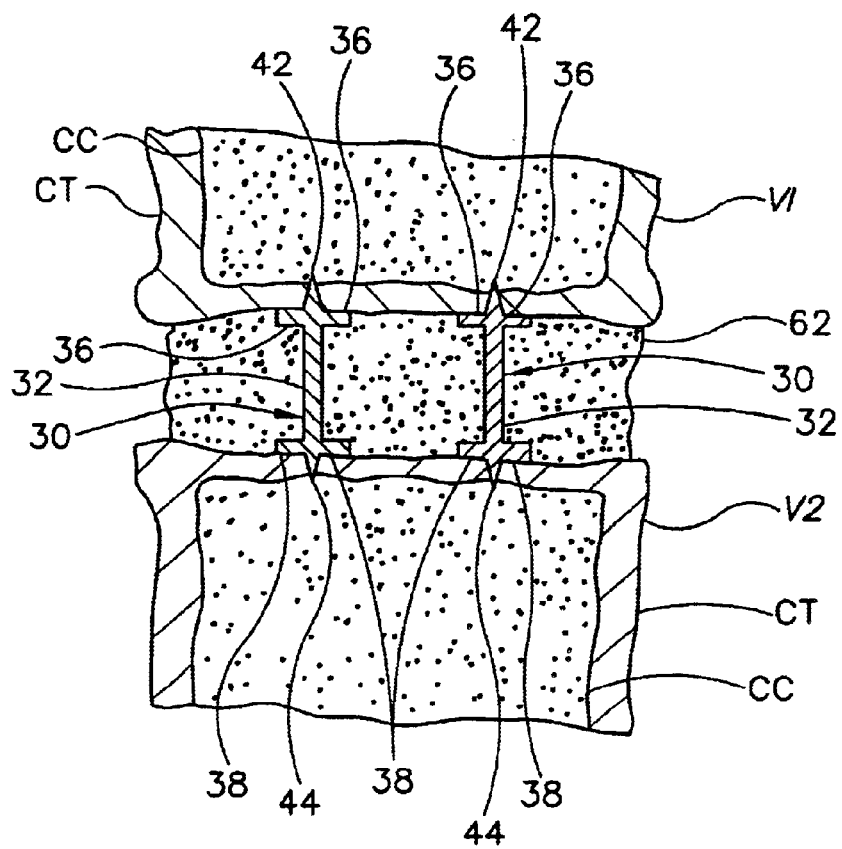
FIG. 3 is a cross section taken in the plane of line 3—3 of FIG. 2 showing two mechanical prostheses and a biological prosthesis between two vertebrae.

As illustrated in FIG. 3, two upper and two lower flex members 36, 38 extend laterally outward from at least one of the first and second faces 32a, 32b of the support 32 for engaging the first and second vertebrae V1, V2, respectively, to distribute load across the vertebrae and thereby to prevent invagination of the support into the soft cancellous bone CC inside the vertebrae. The flex members 36, 38 have stiffness coefficients that are sufficiently small to permit the members to flex elastically toward each other when loaded by the vertebrae V1, V2. The flex members 36, 38 are designed to return to their undeformed positions to restore the selected spacing between the vertebrae V1, V2 when the toad is removed. The upper flex members 36 engage a lower surface of the first vertebra V1 and the lower flex members 38 engage an upper surface of the second vertebra V2. Preferably, the flex members 36, 38 are formed integrally with the support 32. Although the flex members 36, 38 may be longer or shorter without departing from the scope of the present invention, the flex members of the preferred embodiment have lengths which are substantially equal to the length of the support 32. Moreover, the flex members 36, 38 of the preferred embodiment are uninterrupted and continuous, but it is envisioned that they may include holes or cutouts 40 (FIG. 4B) to decrease the total area occupied by the flex members and increase the exposed surface area of the vertebrae V1, V2. Preferably, the flex members 36, 38 have a range of stiffness coefficients between about 250 pounds per inch and about 20,000 pounds per inch (about 450 newton per cm to about 35,400 newton per cm) and more preferably have a coefficient of about 5000 pounds per inch (about 9000 newton per cm), i.e., the flex members flex about 0.08 inches (about 0.20 cm) under a 400 pound (1800 N) load and about 0.02 inches (about 0.05 cm) under a 100 pound (450 N) load. However, the flex members 36, 38 may have other stiffness coefficients without departing from the scope of this invention. Further, the stiffness coefficient may decrease over time as discussed above, so the flex members 36, 38 progressively flex more under repeated loading.

Figure 4A:
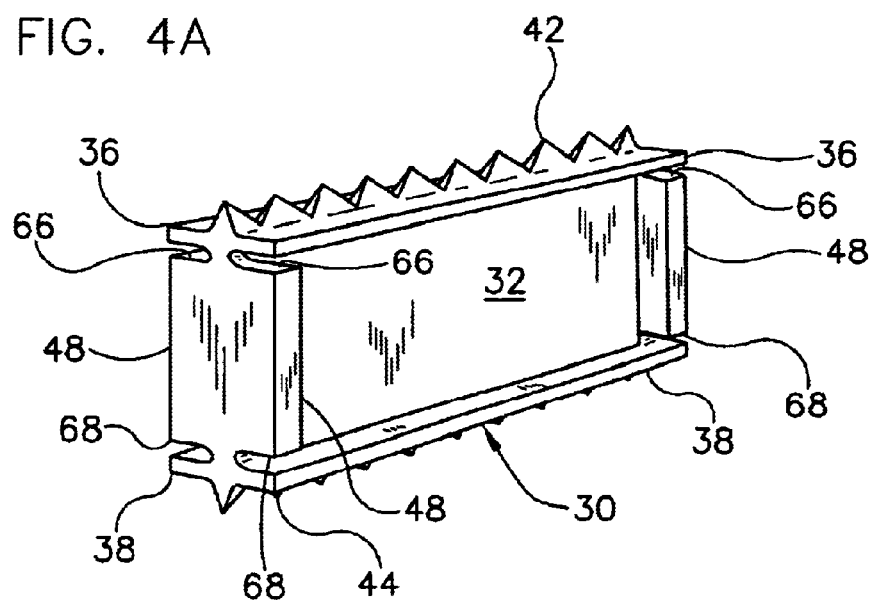
FIG. 4A is a perspective of the mechanical prosthesis.
Figure 4B:
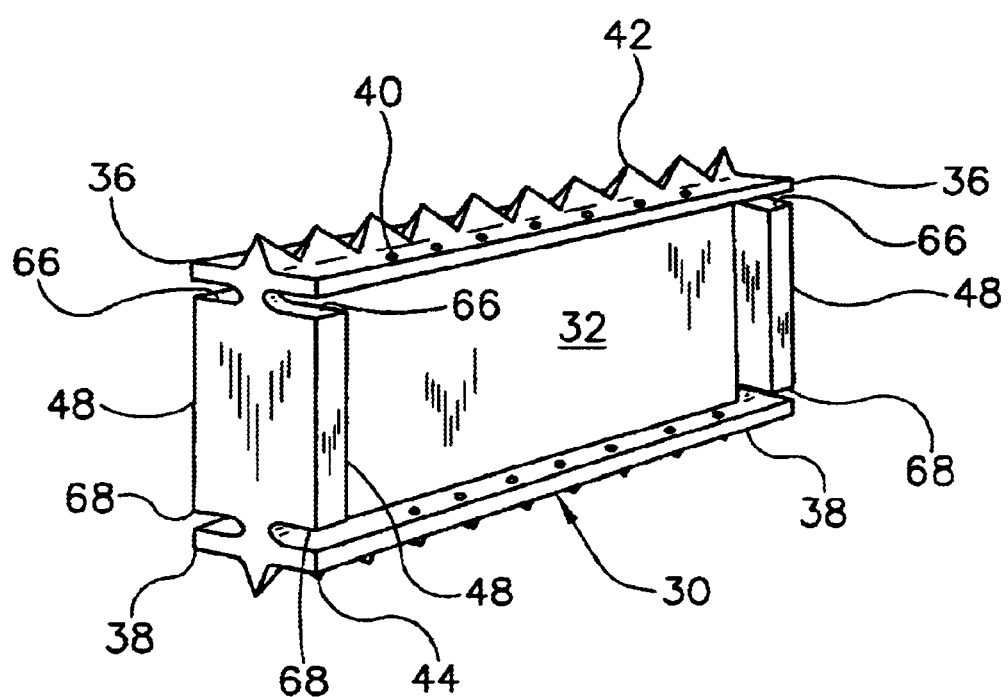
FIG. 4B is a perspective of an alternate embodiment of the mechanical prosthesis.

As illustrated in FIG. 4A, four stiffeners 48 extend laterally from the ends of the support 32 (only three stiffeners are visible) for strengthening the support and for retaining bone graft material 62 (FIG. 3) as will be explained in greater detail below. Although the stiffeners 48 of the preferred embodiment extend from the ends of the support 32 they may be positioned anywhere along the length of the support without departing from the scope of the present invention. It is contemplated that the strengthening function of the stiffeners may not be necessary in all applications. When the anticipated load on the prosthesis is relatively low, such as in the upper spine, the stiffeners may only be needed to retain the bone graft material 62. The stiffeners 48 are preferably integral with the support 32 and have a height less than the height of the support. Although the stiffeners 48 may have other widths without departing from the scope of the present invention, the stiffeners of the preferred embodiment have widths which are substantially equal to the widths of the upper and lower flex members 36, 38. The stiffeners preferably have upper and lower surfaces which constitute upper and lower stops 66, 68, respectively, spaced below and above the upper and lower flex members 36, 38, respectively, to limit flexure of the flex members. Preferably, each flex member 36, 38 and its respective stops 66, 68 are separated by a distance of less than about 0.08 inches (about 0.20 cm).

The upper and lower anchors 42, 44 are positioned at the top and bottom of the support 32, respectively, for anchoring the prosthesis between the first and second vertebrae V1, V2.

The anchors 42, 44 are preferably integral with the support 32 and comprise a plurality of pyramidal members or teeth having sharp points arranged in a straight line. Thus, the anchors 42, 44 provide a sharp serrated edge for preventing movement between the prosthesis 30 and the vertebrae V1, V2. However, it is envisioned that the anchors 42, 44 may have other shapes and patterns without departing from the scope of this invention. Although the anchors 42, 44 of the present embodiment extend the length of the support 32, it is envisioned that they may extend less than the length of the support without departing from the scope of this invention.

As described above, the prosthesis 30 of the preferred embodiment comprises a central support 32, upper and lower flex members 36, 38, upper and lower anchors 42, 44 and stiffeners 48. However, it is envisioned that fewer than all of these components may be used in the prosthesis without departing from the scope of the present invention. For instance, the prosthesis may comprise only a central support and upper and lower flex members, or a central support and upper and lower anchors, or a central support and stiffeners.

As illustrated in FIG. 1, the height of one end of the support may be taller than the height of the other end. This height difference orients the vertebrae V1, V2 at an angle with respect to each other for restoring curvature to the spine S. For instance, kyphotic curvature is achieved by inserting the prosthesis 30 so that the taller end is positioned toward the back of the spine and the shorter end is positioned toward the front of the spine. Reversing the position of the prosthesis so that the taller end is positioned toward the front of the spine increases lordotic curvature as illustrated in FIG. 1. Moreover, the prosthesis may be used in combination with a second prosthesis having a different height to correct scoliotic deformities by reversing and supporting the angle of inclination. In a second embodiment (not shown), the support is substantially rectangular and does not angle the first vertebra V1 relative to the second vertebra V2.

Referring to FIG. 3, the bone graft material or biological prosthesis 62 of the prosthetic system is positioned in the space between the vertebrae V1, V2 to promote bone and blood vessel growth between the vertebrae. The graft material 62 may be composed of any of several types of biological tissue, including combinations of crushed and/or cultured cancellous bone, hydroxyapatite, and bioengineered cancellous-like structures composed of inorganic or organic salts. Preferably, the bone or other biological tissue is ground into particles having a desired size (e.g., particles having a 1 mm screen size) and mixed with a solvent to form a solution in which the bone or tissue is suspended. This mixture permits delivery of the graft material 62 and allows the graft material to conform to the available space between vertebrae V1, V2. When cancellous bone is used, it may be harvested from the patient or another donor. The solvent used to form the solution may be an inorganic or organic solvent which aids in delivering the graft and serves as an adhesive that hardens the solution into a semisolid or solid state after being inserted between the vertebrae. Preferably, the solvent polymerizes on exposure to air or biological tissue, upon the addition of a polymerizing enzyme, or upon changing its temperature. The solvent may be removed after the graft material is inserted, or it can be a component of the tissue which remains after insertion to promote bone and blood vessel growth. Although other solvents may be used without departing from the scope of the present invention, the solvent of the preferred embodiment is made from hyaluronic acid and gellan (e.g., carrageenan). The solvent may also include alginate and/or xanthan.

In addition, factors for stimulating osteogenesis are preferably added to the bone graft material 62. Examples of such factors include bone morphogenic proteins, transforming growth factor-B, insulin-like growth factor or Somatomedin-C, platelet derived growth factors, fibroblast growth factors and tumor necrosis factors. These exemplary factors are not exhaustive, and it is contemplated that other factors may be used. Further, the bone graft material 62 preferably includes synthetic angiogenic factors or biological tissue-derived angiogenic factors.

Figure 5:
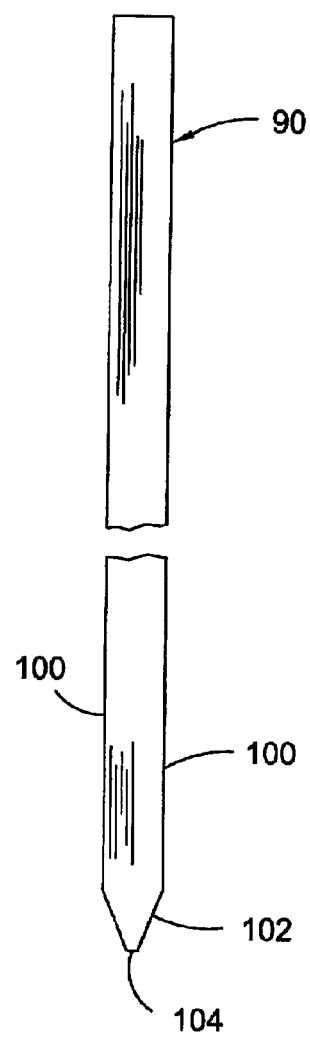
FIG. 5 is a front elevation of a spacer of the present invention.
Figure 6:
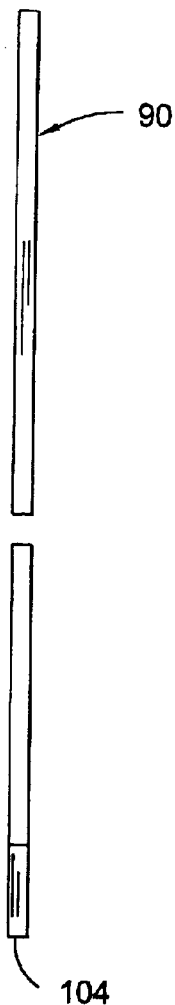
FIG. 6 is a side elevation of the spacer of FIG. 5.

Referring to FIGS. 5–11, a set of surgical instruments for inserting the prosthetic system (i.e., the mechanical prosthesis 30 and the biological prosthesis 62) comprises a spacer, a guard and cutting tool (generally designated 90, 92 and 94, respectively). As shown in FIGS. 5 and 6, the spacer 90 is an elongate bar having opposing surfaces 100 for engaging the facing surfaces of the first and second vertebrae V1, V2 to space the vertebrae by a selected distance. Although the spacer 90 may have other dimensions without departing from the scope of the present invention, the spacer of the preferred embodiment is about 12–17 cm (about 5–7 inches) long, about 6 to about 14 mm (about 0.2–0.5 inches) wide and about 0.2 cm (about 0.08 inches) thick. The preferred length enables the spacer to protrude from the patient after insertion between the vertebrae so it may be grasped by a surgeon for manipulation. Further, the thickness of the spacer 90 of the preferred embodiment minimizes the amount of tissue that must be removed from between and around the vertebrae V1, V2 to accommodate the spacer. The spacer 90 has a tapered tip 102 for facilitating insertion of the spacer between the first and second vertebrae V1, V2. The tapered tip 102 is typically about 1–3 cm (about 0.5–1.5 inches) long and tapers from the opposing surfaces 100, to a blunt end 104 which is, for instance, about 0.3 cm (about 0.1 inches) wide. However, these dimensions may vary depending upon the pre-insertion space between the vertebrae V1, V2 and the height of the prosthesis 30.

As will be appreciated by those skilled in the art, the opposing surfaces 100 orient the vertebrae V1, V2 at an angle or parallel to each other. In the embodiment illustrated in FIG. 17, the opposing surfaces 100 are parallel so they orient the facing surfaces of the vertebrae parallel to each other. FIG. 18 illustrates a second embodiment of the spacer 90' having opposing surfaces 100' which are angled with respect to each other for orienting the vertebrae V1, V2 at an angle relative to each other. In all other respects, the spacer 90' of the second embodiment is identical to that of the first embodiment and will not be described in further detail.

Figure 7:
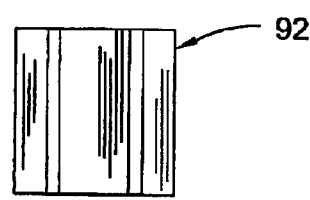
FIG. 7 is a front elevation of a guard of the present invention.
Figure 8:
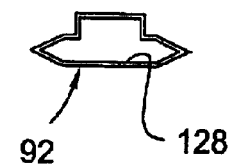
FIG. 8 is a bottom plan of the guard.

Referring to FIGS. 7 and 8, the guard 92 is a tube having a passage sized and shaped for simultaneously receiving the spacer 90 and the cutting tool 94 as will be explained in greater detail below. Although the guard 92 may have other lengths without departing from the scope of this invention, the guard of the preferred embodiment is approximately 3–10 cm (about 1–4 inches) long. The guard 92 prevents the cutting tool 94 from errantly cutting surrounding tissue as the tool is inserted between the vertebrae V1, V2.

Figure 21:
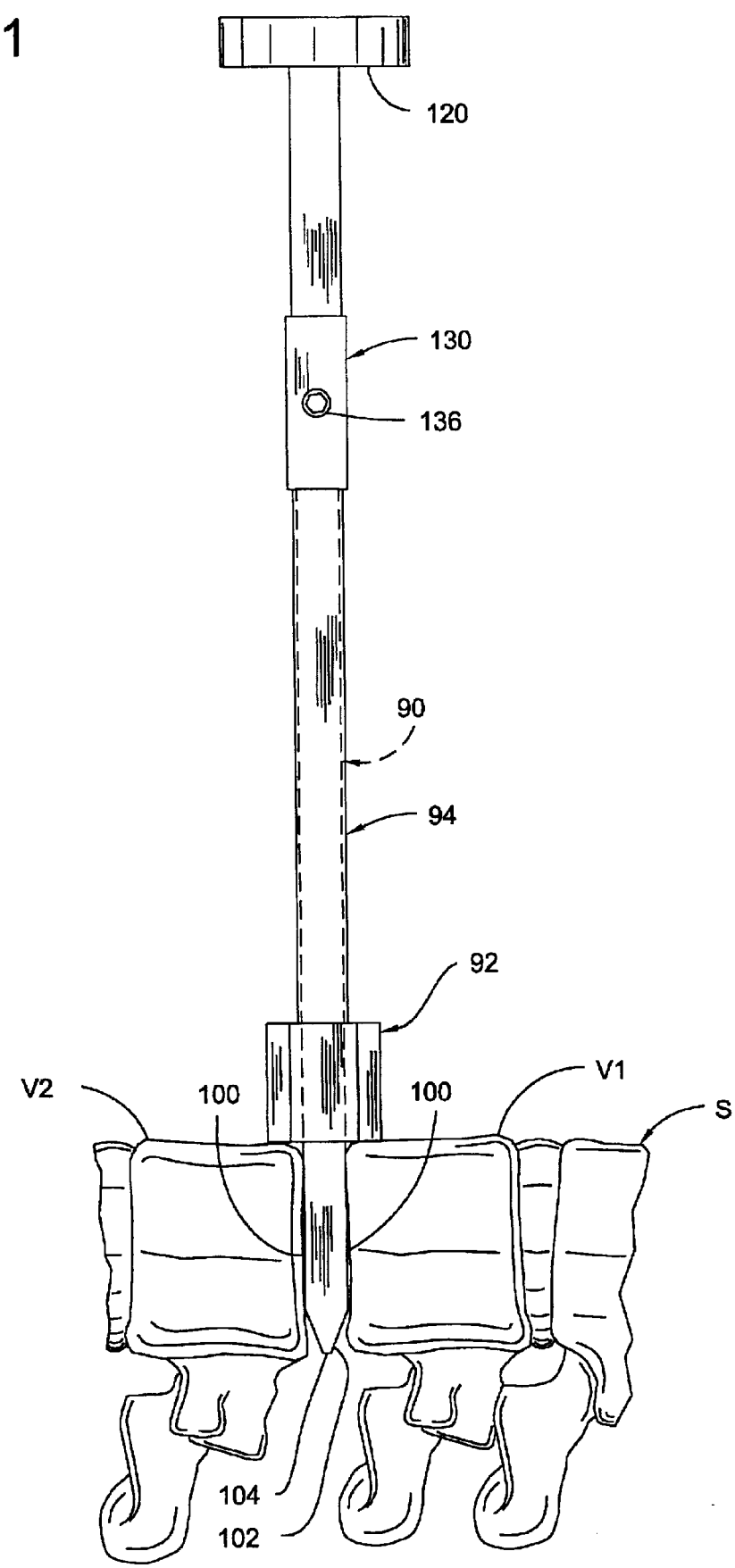
FIG. 21 is an elevation similar to FIG. 20 showing the depth gauge installed on the cutting tool.

Referring to FIGS. 9–11, a cutter 114 having opposing blades 116 is provided at one end of the cutting tool 94 for simultaneously cutting grooves in the facing surfaces of the first and second vertebrae V1, V2. A rectangular shaft 118 extends from the cutter 114 to a head 120 at an opposite end of the tool 94 for driving the cutter between the vertebrae V1, V2 with a mallet (not shown). Although the blades 116 may have other lengths without departing from the scope of the present invention, the blades of the preferred embodiment are about 1–4 cm (about 0.5–1.5 inches) long. As illustrated in FIG. 21, the blades 116 are preferably sized to simultaneously cut grooves which extend through the cortical bone CT and into the cancellous bone CC of each vertebra. As will be appreciated by those skilled in the art, the edges of the blades 116 are spaced by a distance slightly larger than the distance between the anchors 42, 44 of the mechanical prosthesis 30 so that the prosthesis can easily be positioned between the vertebrae V1, V2 before removing the spacer 90. The leading corners 122 of the blades 116 are rounded to center the blade between the vertebrae and improve cutting.

Figure 12:
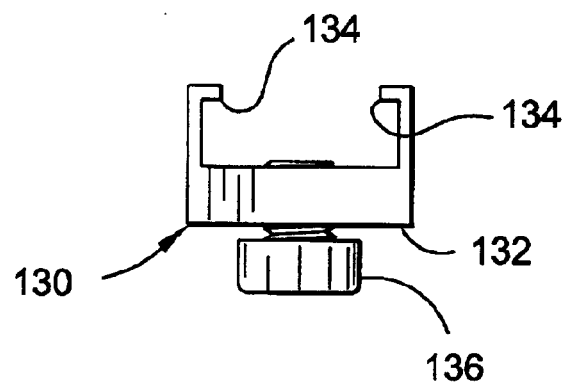
FIG. 12 is a top plan of a depth gauge of the present invention.
Figure 13:
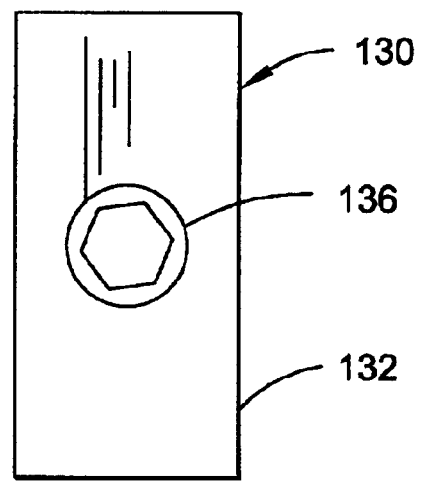
FIG. 13 a front elevation of the depth gauge.

As illustrated in FIG. 12, a depth gauge is generally designated by 130. As will be explained in greater detail below, the gauge 130 is releasably attachable to the cutting tool 94 to visually indicate when the grooves cut in the vertebrae V1, V2 have appropriate lengths. The gauge 130 comprises a body 132 having a length equal to the appropriate lengths of the grooves in the vertebrae, two hooked arms 134 for engaging opposite surfaces of the cutting tool shaft 118 and a set screw 136 for holding the gauge in position on the cutting tool 94.

Figure 14:
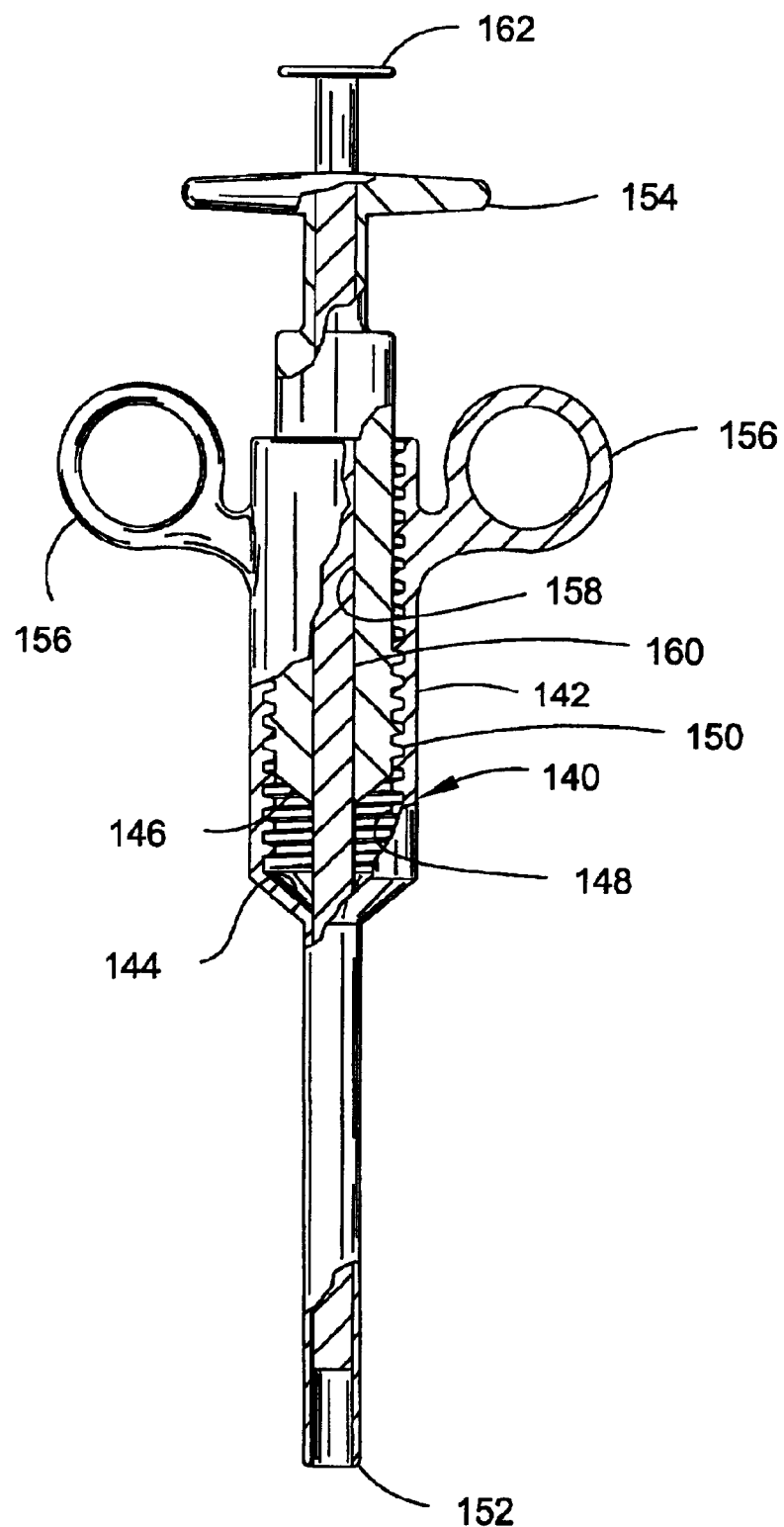
FIG. 14 is a front elevation in partial section of a syringe of the present invention.

Referring to FIG. 14, a syringe for injecting the bone graft material 62 between the first and second vertebrae V1, V2 is generally designated by 140. The syringe 140 comprises a cylindrical body 142 having a hollow interior 144 and a piston 146 received in the hollow interior. The interior surface of the hollow interior 144 and the exterior surface of the piston 146 have interengaging threads 148, 150, respectively, so the piston advances or retracts in the hollow interior of the cylindrical body 142 as the piston is rotated relative to the body. A nozzle 152 at one end of the cylindrical body 142 delivers bone graft material 62 from the hollow interior 144 to a space between the first and second vertebrae V1, V2 as the piston 146 advances toward the nozzle. A handle 154 attached to the piston 146 and loops 156 extending from the body 142 facilitate rotation of the piston relative to the body. A hole 158 extends through the piston 146 for receiving a cylindrical plunger 160. The plunger 160 is free to reciprocate in the hole 158 and through the nozzle 152 to force material through the nozzle when the piston 146 is fully advanced. A head 162 provided on the end of the plunger 160 limits the travel of the plunger and aids in pushing the plunger. As will be understood by those skilled in the art, relatively viscous graft material 62 may be delivered to an implantation site by placing it in the hollow interior 144 of the body 142 and rotating the piston to squeeze the material through the nozzle. In an alternate embodiment (not shown), the interior of the cylinder body 142 and the exterior of the piston 146 may be smooth (i.e., the threads may be omitted) so that the graft material is squeezed through the nozzle 152 by pushing the piston toward the nozzle.

Figure 15:
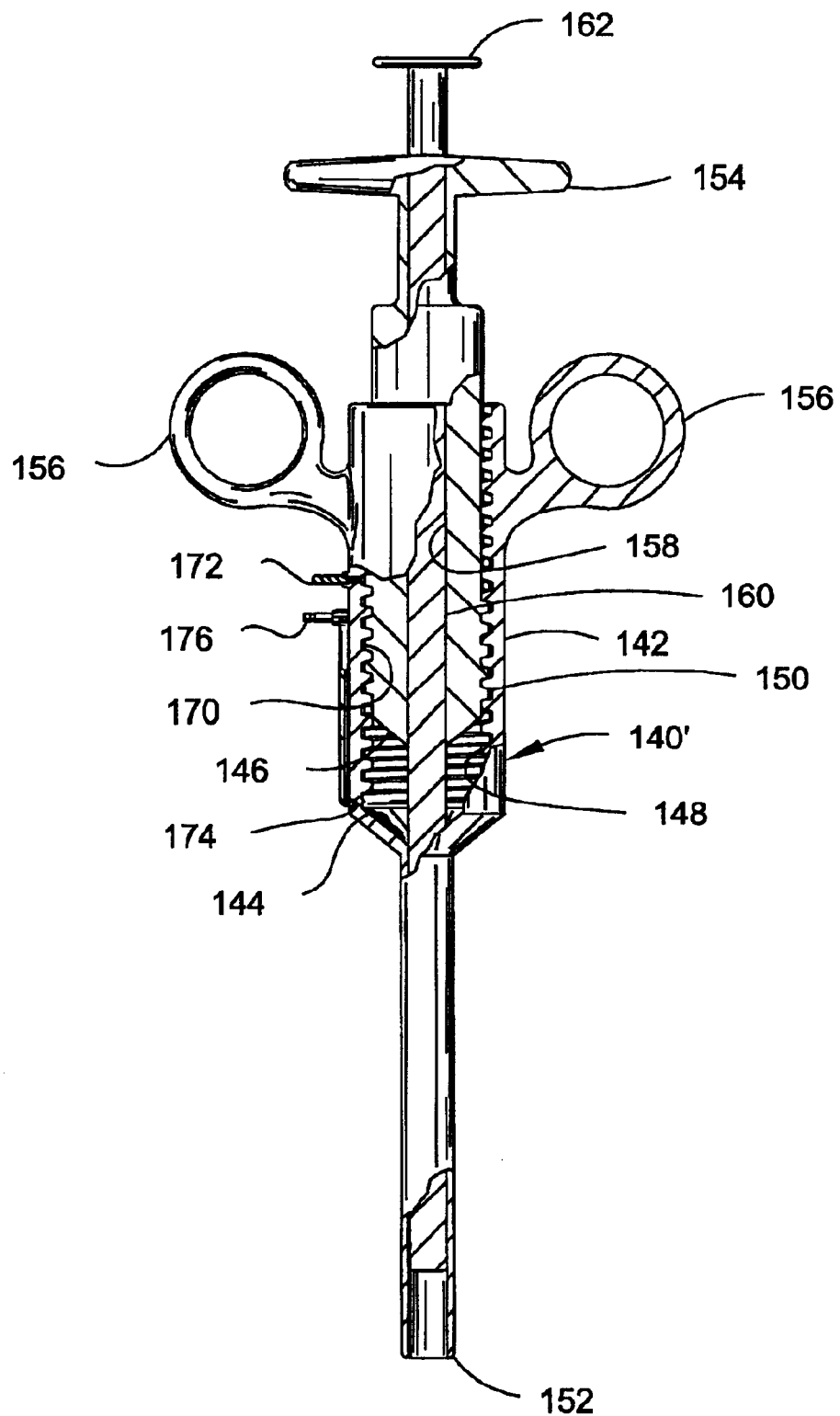
FIG. 15 is a front elevation in partial section of a second embodiment of a syringe of the present invention.
Figure 16:
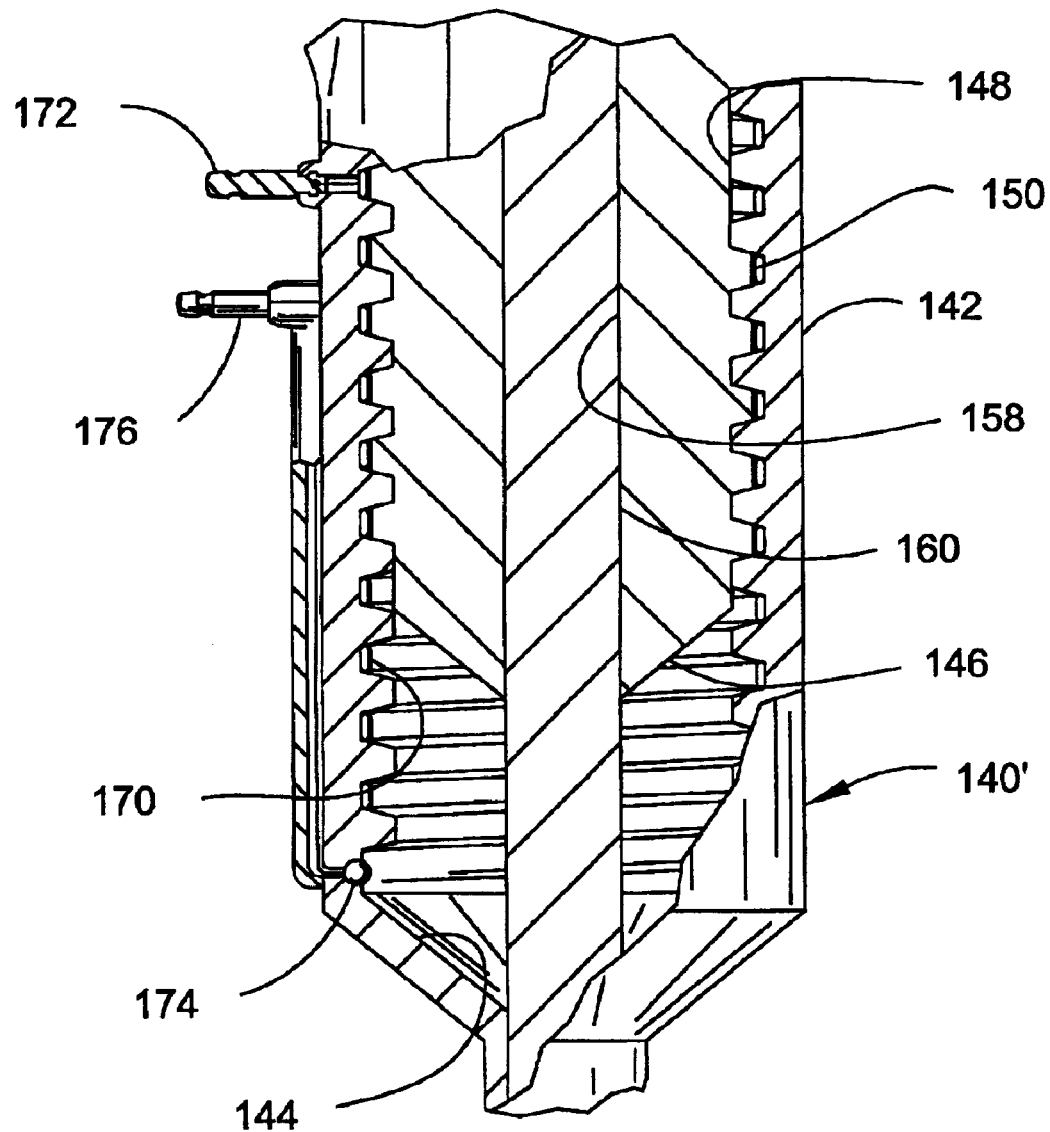
FIG. 16 is an enlarged, fragmentary front elevation in partial section of the second embodiment of the syringe.

Referring to FIGS. 15 and 16, a syringe of a second embodiment, generally designated 140', is identical to the syringe 140 of the first embodiment except that it comprises a heating element 170 for heating bone graft material 62 held in the interior 144 of the body 142 to reduce its viscosity so it is easier to push through the nozzle 152. Although the heating element 170 may have other configurations without departing form the scope of the present invention, in the preferred embodiment the heating element is a coil sized to fit between the threads 148 of the cylindrical body 142. A pin 172 (only one of which is visible in FIG. 15) is provided at each end of the heating element 170 for connecting the element to an electrical power source (not shown). Preferably, the syringe 140' includes a temperature sensor 174 (e.g., a thermocouple) positioned in the hollow interior 144 of the body 142 near the nozzle 152 for measuring the temperature of the bone graft material 62. A second set of pins 176 (only one of which is visible in FIG. 15) is connected to the temperature sensor 174 for connecting the sensor to a controller (not shown) for controlling the heating element 170. Although the temperature to which the graft material 62 is heated will vary according to the composition of the material, it is envisioned that in a preferred embodiment, the control will maintain the temperature of the material between about 20° C. and about 40° C. (about 70° F.–100° F.). Although other materials may be used without departing from the scope of the present invention, the surgical instruments (i.e., the spacer 90, the guard 92, the cutting tool 94 and the syringe 140) of the preferred embodiment are made of surgical steel. Alternatively, the syringe 140 may be made of plastic.

A surgical method of inserting the prosthetic system between the first and second vertebrae V1, V2 to limit motion between and to facilitate fusion of the vertebrae will now be described. The method comprises the steps of exposing the first and second vertebrae V1, V2, excising at least a portion of a disc (not shown) from between the first and second vertebrae, and scraping cartilage (not shown) from facing surfaces of the vertebrae to expose the facing surfaces. The method may be performed either from the front or the back depending on which vertebrae are being exposed. For instance, if vertebrae in the lower back are being exposed, the incision is normally made from the back, but if vertebrae in the neck are being exposed, the incision is normally made from the front. Preferably, a substantial portion of the interior of the disc is excised to permit insertion of the tools and prosthetic system. Removing the cartilage from the bone increases the speed and efficacy of the fusion because bone growth initiates at the exposed surfaces of the vertebrae. Generally, these steps are well known in the art and therefore no further description is necessary.

Figure 17:
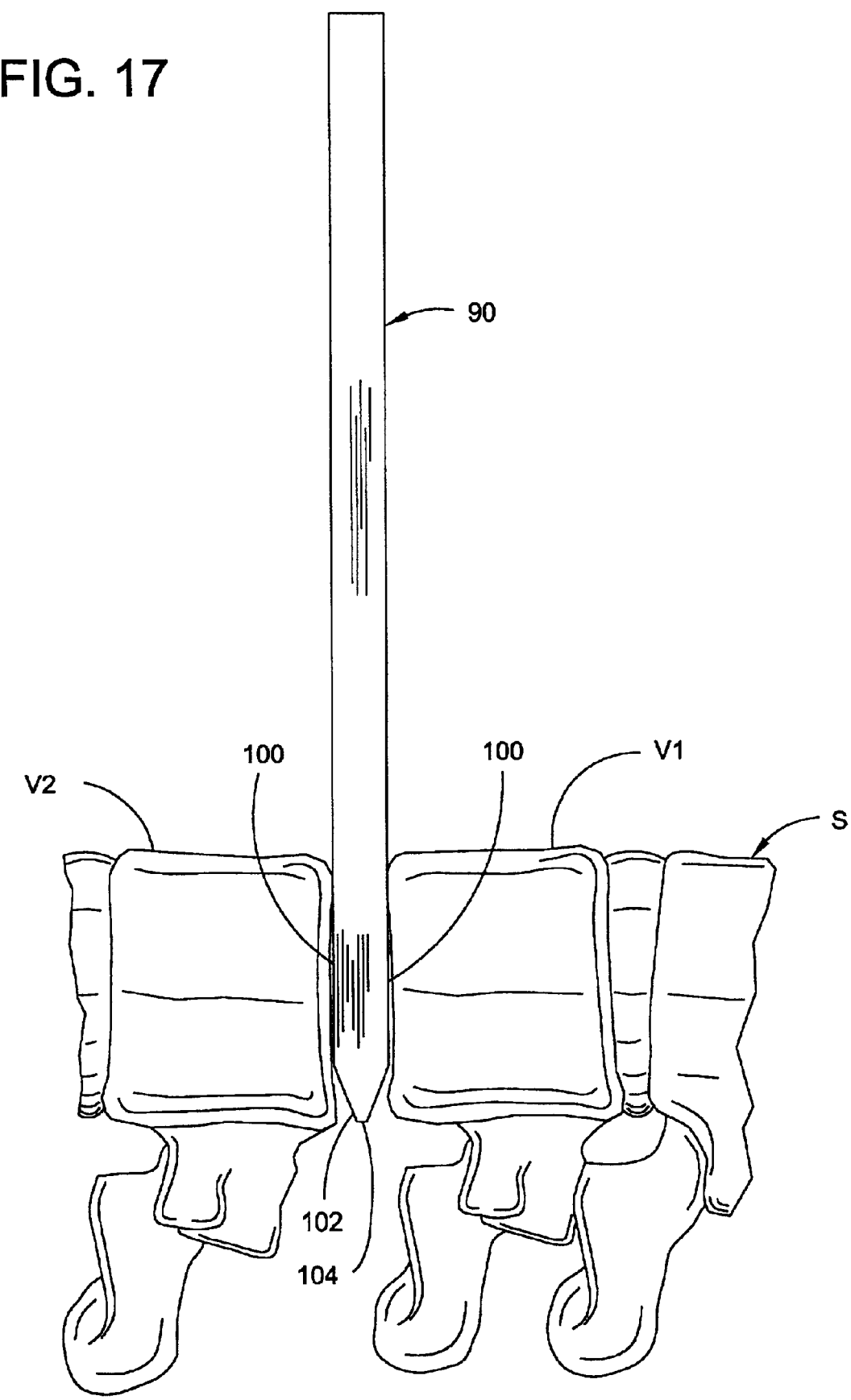
FIG. 17 is a side elevation of the spacer of FIG. 5 shown inserted between vertebrae of a spine.
Figure 18:
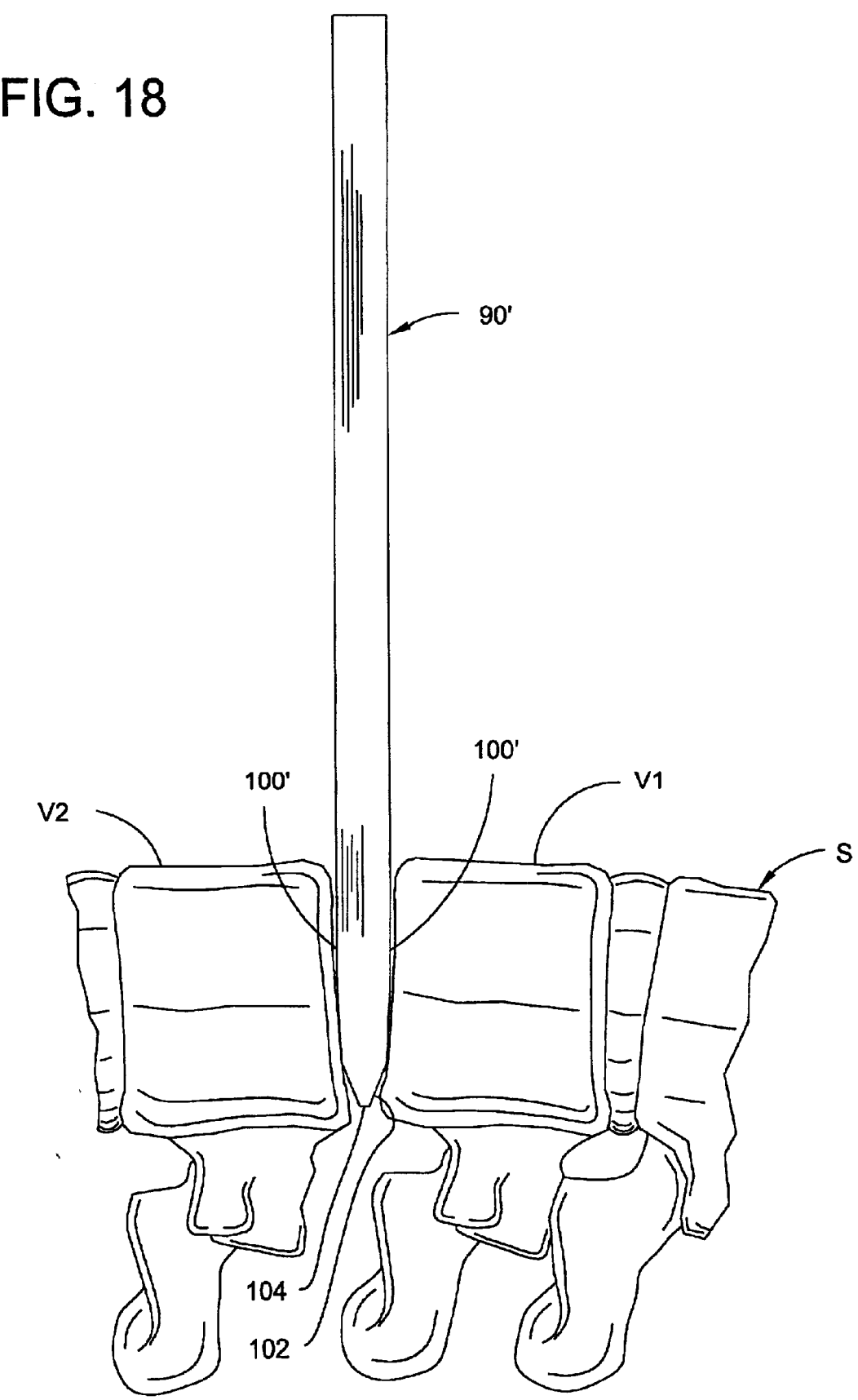
FIG. 18 is a side elevation of a second embodiment of a spacer of the present invention shown inserted between vertebrae.
Figure 19:
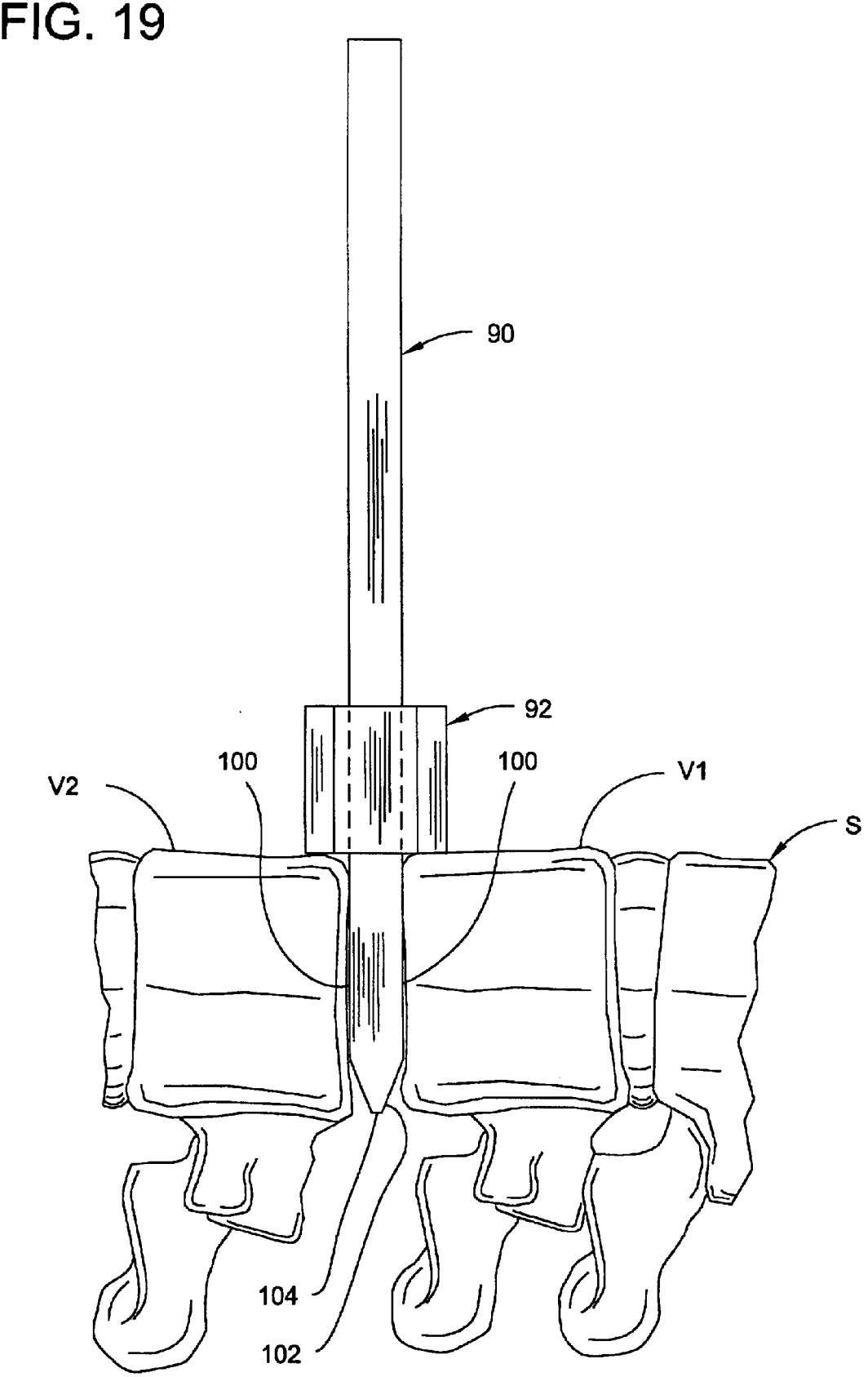
FIG. 19 is an elevation similar to FIG. 17 showing the guard engaging the spacer.
Figure 20:
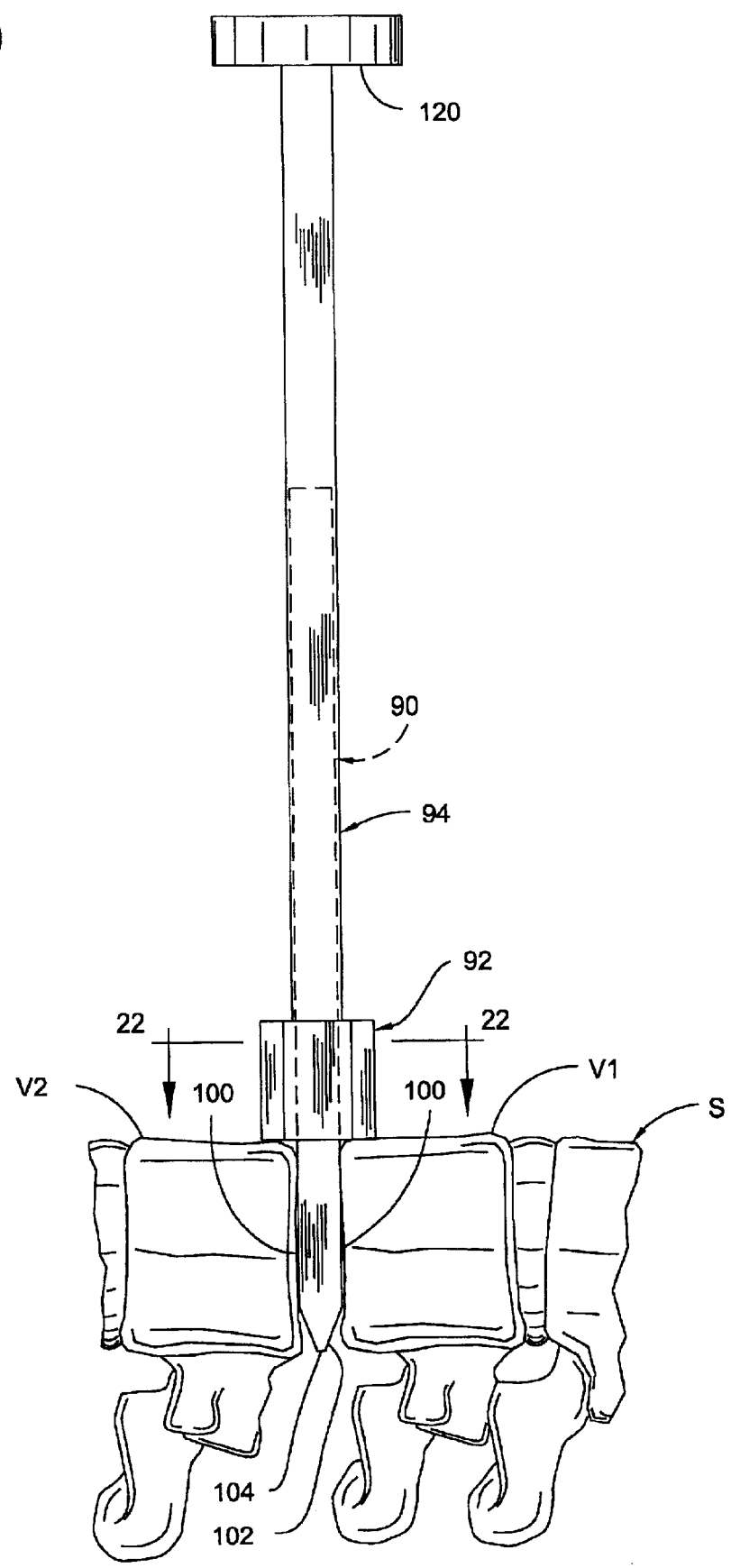
FIG. 20 is an elevation similar to FIG. 19 showing the cutting tool received in the guard.
Figure 22:
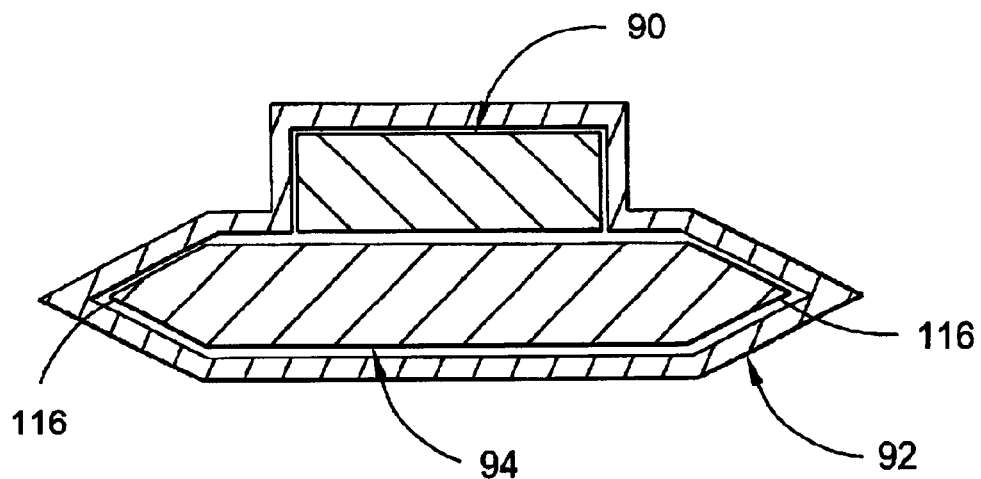
FIG. 22 is a cross section taken in the plane of line 22—22 in FIG. 21.
Figure 24:
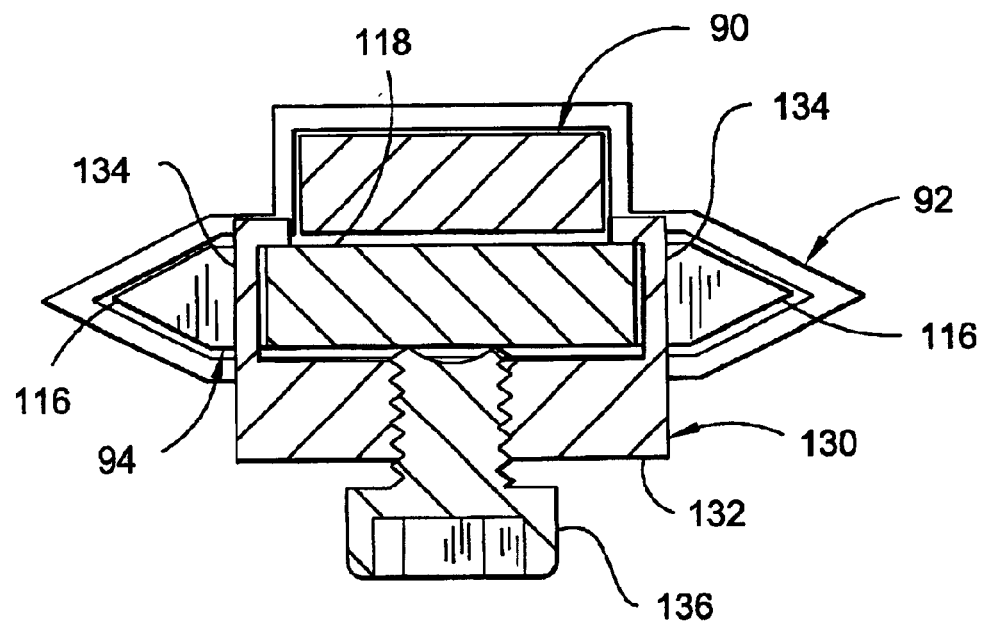
FIG. 24 is a cross section taken in the plane of line 24—24 in FIG. 23.
Figure 23:
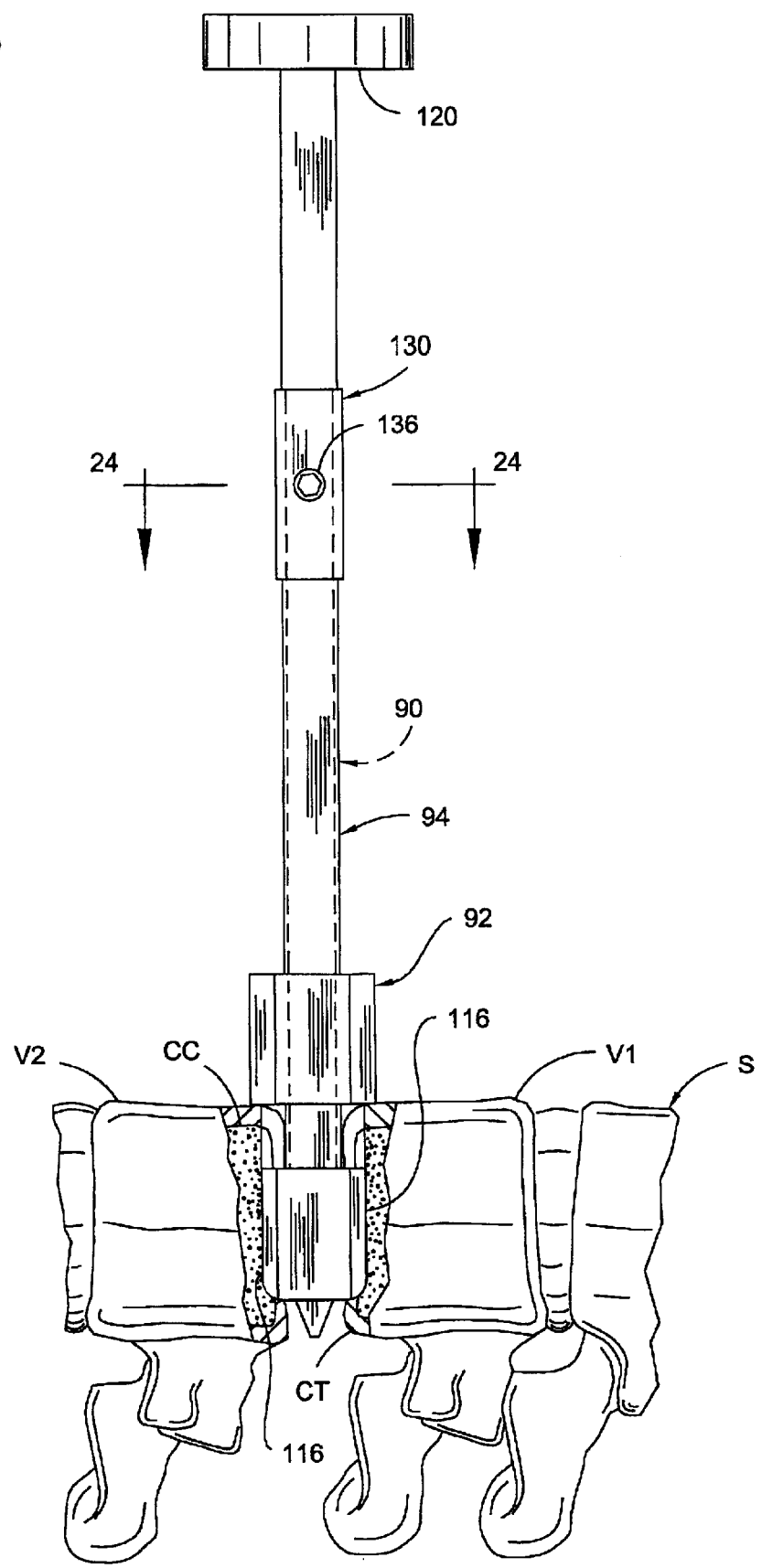
FIG. 23 is an elevation similar to FIG. 21 showing the cutting tool advanced between the vertebrae.

Once the vertebrae have been exposed and the facing surfaces scraped, the first and second vertebrae V1, V2 are spaced by the selected distance by inserting the spacer 90 between the vertebrae as shown in FIG. 17. As previously explained, the vertebrae may be oriented either parallel or at an angle with respect to each other by alternately inserting a spacer 90 having parallel surfaces 100 or a spacer 90' having angled surfaces 100' as shown in FIG. 18. If needed, the spacer 90 may be tapped on its end with a mallet to position it between the vertebrae V1, V2. Once the spacer 90 is seated, the guard 92 is slid over the spacer until its lower end rests on the vertebrae V1, V2. The guard 92 is positioned so that spacer 90 is oriented with respect to the guard as shown in FIG. 22 and the blades 116 of the cutting tool 94 are inserted into the interior of the guard. As will appreciated by those skilled in the art, the guard 92 guides the cutting tool 94 toward the desired implantation site and prevents the blades 116 of the cutter 114 from errantly cutting tissue surrounding the vertebrae V1, V2. The depth gauge 130 is installed on the cutting tool 94 by engaging the hooked arms 134 around opposite surfaces of the cutting tool shaft 118 as shown in FIG. 24. The lower end of the depth gauge 130 is aligned with the upper end of the spacer 90 and the set screw 136 is tighten to hold the gauge in position on cutting tool 94 as illustrated in FIG. 21. The head 120 of the cutting tool 94 may be tapped with a mallet (not shown) to drive the cutting tool between the vertebrae V1, V2 until the upper end of the depth gauge 130 is aligned with the upper end of the spacer 90 as illustrated in FIG. 23. As explained above, the grooves formed by the cutting tool 94 penetrate through the cortical bone CT into the cancellous bone CC of the vertebrae V1, V2. Once the grooves are cut in the vertebrae V1, V2, the cutting tool 93 and the guard 92 may be removed to expose the grooves. A suitably sized mechanical prosthesis 30 may then be inserted between the vertebrae V1, V2 as shown in FIG. 1 before removing the spacer 90. In the preferred embodiment, the prosthesis 30 is placed between the vertebrae V1, V2 by gripping it with a suitable instrument and sliding it into the grooves.

Preferably, several spacers 90, cutting tools 94, and mechanical prostheses 30 are provided in a kit so that different selected spacings may be obtained between vertebrae. For instance, once a selected vertebral spacing is chosen, the appropriately sized spacer 90, cutting tool 94 and mechanical prosthesis 30 may be chosen from the kit to achieve the selected spacing.

Figure 2:
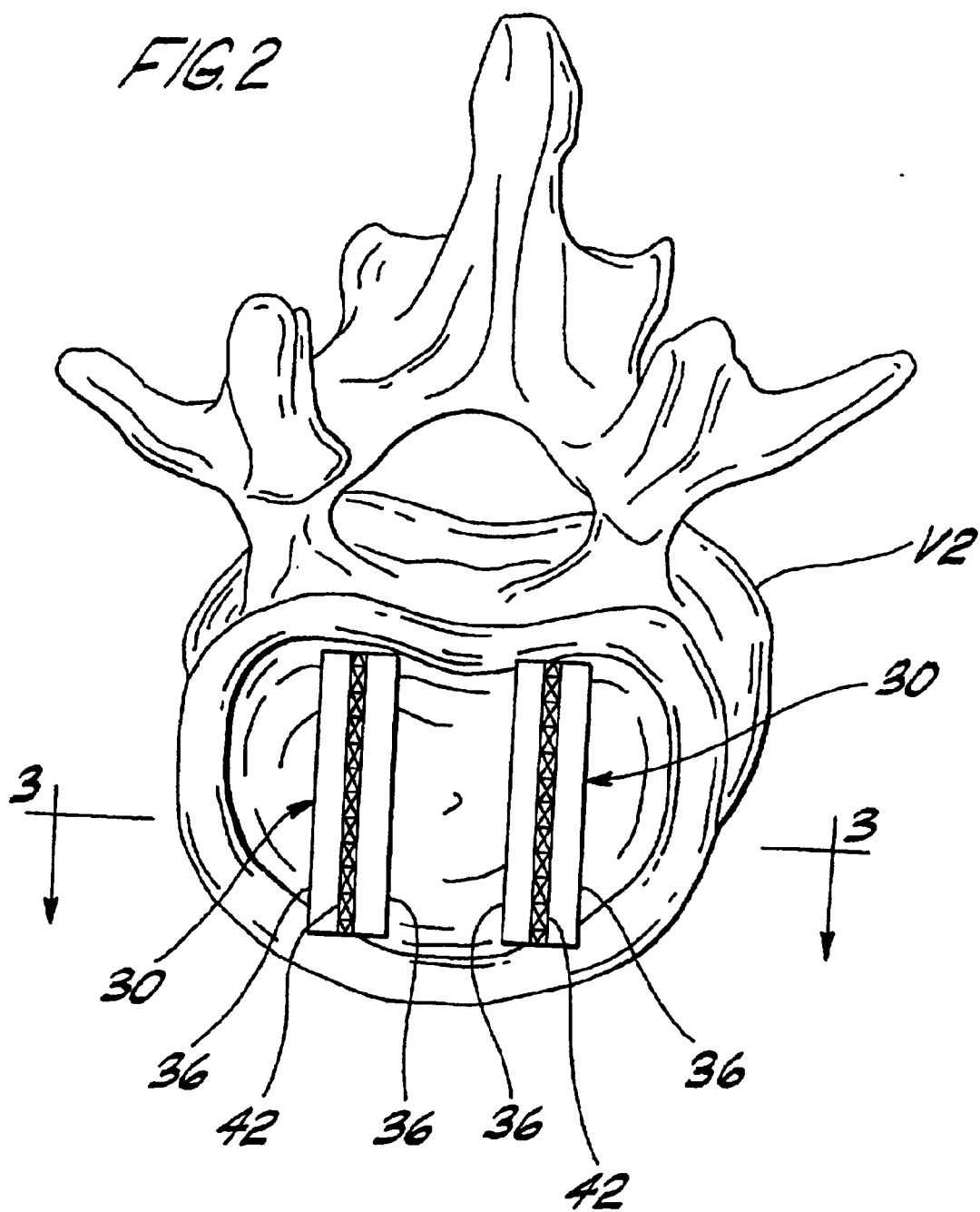
FIG. 2 is a top plan of two mechanical prostheses shown in relation to a vertebra.

As will be apparent to those skilled in the art, the procedure described above may be repeated to insert a second mechanical prosthesis between the first and second vertebrae V1, V2, as shown in FIG. 2. Once the mechanical prostheses 30 are inserted on each side of a midline of the spine S, bone graft material may be packed between the vertebrae V1, V2 and around the mechanical prostheses to promote bone growth between and facilitate fusion of the vertebrae. The packing step is performed by filling the interior 144 of the syringe 140 with bone graft material 62 and screwing the piston 146 into the body 142 until the graft material 62 is expelled from the nozzle 152. The surgeon guides the syringe 140 as the graft material is expelled from the nozzle 152 to inject the material between the vertebrae V1, V2. The plunger 156 may be advanced into the nozzle 152 to push any remaining graft material 62. Preferably and as illustrated in FIG. 3, the bone graft material 62 is injected between the vertebrae V1, V2 until it fills the entire space between the vertebrae.

As described above, the prosthetic system of the present invention has several advantages over prior art systems. For instance, the flexibility of the mechanical prosthesis 30 and in particular the flexibility of the upper and lower flex members 36, 38 allow the vertebrae V1, V2 to apply loads to the bone graft material 62. According to Wolff's law, loading the bone graft material 62 stimulates bone growth. Further, the prosthetic system produces less trauma because the mechanical prosthesis 30 and the instruments for implanting the prosthesis are relatively narrow. The relative narrow width of the prosthesis 30 also permits larger areas of the facing surfaces of the vertebrae V1, V2 to be exposed to improve bone growth and the overall success of the prosthetic system.

As will be appreciated by those skilled in the art, the prosthetic system and method of the present invention are usable across more than one intervertebral space. The height of the prosthesis may be expanded to span two or more intervertebral spaces and the intervening vertebrae. Further, the system and method of the present invention may be used for vertebrae at any level of the spine, i.e., cervical, thoracic or lumbar.

Finally, the instruments of the present invention allow the prosthetic system to be positioned more efficiently and more accurately. The cutting tool 94 cuts both facing surfaces of the vertebrae V1, V2 at the same time, so that the surgeon spends less time cutting and so that the prosthesis 30 is precisely positioned upon insertion. Further, the syringe 140 allows viscous bone graft materials to be accurately inserted in the space between vertebrae with minimal effort. As those skilled in the art will appreciate, these features result in less trauma and increase the likelihood of success of the surgery.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A spinal prosthesis for insertion during surgery in a space between first and second vertebrae of a spine of a patient to limit motion between said first and second vertebrae and/or to facilitate fusion of said first and second vertebrae, said prosthesis comprising:

a vertical support sized and shaped for insertion between said first and second vertebrae, said support having a height measured between a top and a bottom approximately equal to a selected spacing between said first and second vertebrae, upper and lower flex members monolithically formed with and extending from the top and bottom of the support, respectively, for engaging said first and second vertebrae, said upper and lower members having a stiffness sufficiently small to permit the members to flex elastically toward each other under loading from said first and second vertebrae, said upper and lower flex members having lengths substantially equal to a length of the support.

2. A spinal prosthesis for insertion during surgery in a space between first and second vertebrae of a spine of a patient to limit motion between said first and second vertebrae and/or to facilitate fusion of said first and second vertebrae, said prosthesis comprising:

a vertical support sized and shaped for insertion between said first and second vertebrae, said support having a height measured between a top and a bottom approximately equal to a selected spacing between said first and second vertebrae, said support being generally laterally centered on the prosthesis;

at least one stiffener extending from the support for strengthening the support; and upper and lower flex members monolithically formed with and extending from the top and bottom of the support, respectively, for engaging said first and second vertebrae, said upper and lower members having a stiffness sufficiently small to permit the members to flex elastically toward each other under loading from said first and second vertebrae.

3. A spinal prosthesis as set forth in claim 2 wherein the stiffener has a width which is substantially equal to a width of said upper flex member and substantially equal to a width of said lower flex member.

4. A spinal prosthesis for insertion during surgery in a space between first and second vertebrae of a spine of a patient to limit motion between said first and second vertebrae and/or to facilitate fusion of said first and second vertebrae, said prosthesis comprising:

a vertical support sized and shaped for insertion between said first and second vertebrae, said support having a height measured between a top and a bottom approximately equal to a selected spacing between said first and second vertebrae, said support being generally laterally centered on the prosthesis;

upper and lower flex members monolithically formed with and extending from the top and bottom of the support, respectively, for engaging said first and second vertebrae, said upper and lower members having a stiffness sufficiently small to permit the members to flex elastically toward each other under loading from said first and second vertebrae; and upper and lower stops positioned adjacent said upper and lower flex members, respectively, for limiting flexure of the members toward each other.

5. A spinal prosthesis as set forth in claim 4 wherein the support is non-collapsible under loading provided by said first and second vertebrae.

6. A spinal prosthesis as set forth in claim 4 wherein the support constitutes the only longitudinal support of the prosthesis.

7. A spinal prosthesis as set forth in claim 6 wherein said support is a generally quadrilateral panel having opposite first and second faces, each upper and lower flex member extending laterally from at least one of the first and second faces.

8. A spinal prosthesis as set forth in claim 4 wherein said support is a generally quadrilateral panel having opposite first and second faces, each upper and lower flex member extending laterally from the first and second faces.

9. A spinal prosthesis as set forth in claim 4 further comprising at least one stiffener extending from the support for strengthening the support.

10. A spinal prosthesis as set forth in claim 9 further comprising upper and lower anchors positioned at said top and bottom of the support, respectively, for anchoring the support between said first and second vertebrae.

11. A spinal prosthesis as set forth in claim 4 further comprising upper and lower anchors positioned at said top and bottom of the support, respectively, for anchoring the support between said first and second vertebrae.

12. A spinal prosthesis as set forth in claim 4 wherein the support has opposite first and second ends, and said first end is taller than said second end to angle said first vertebra relative to said second vertebra.

13. A spinal prosthesis as set forth in claim 4 wherein said upper and lower stops are spaced less than about 0.08 inches from said upper and lower flex members, respectively, when said members are unflexed thereby limiting flexure of said upper and lower flex members to less than about 0.08 inches.

14. A spinal prosthesis as set forth in claim 4 wherein said upper and lower flex members have openings therethrough to decrease the total area occupied by the flex members and increase the exposed surface area of the vertebrae.

15. A spinal prosthesis as set forth in claim 4 wherein said upper and lower flex members have stiffness coefficients of between about 250 pounds per inch and about 20,000 pounds per inch.

16. A spinal prosthesis as set forth in claim 15 wherein said upper and lower flex members have stiffness coefficients of about 5000 pounds per inch.

17. A spinal prosthesis as set forth in claim 4 wherein the upper and lower flex members have a stiffness which decreases over time after the prosthesis is inserted in the spine.

18. A spinal prosthesis as set forth in claim 17 wherein said prosthesis is absorbable by said patient.

19. A spinal prosthesis as set forth in claim 17 wherein said prosthesis is nonabsorbable by said patient.

20. A spinal prosthesis as set forth in claim 4 having a compressive strength of at least about 8000 newtons.

21. A spinal prosthesis as set forth in claim 4 further comprising upper and lower anchors positioned at said top and bottom of the support, respectively, for anchoring the support between said first and second vertebrae.

22. A spinal prosthesis as set forth in claim 21 wherein each of said upper and lower anchors includes a sharp edge for holding the respective anchor in position with respect to the respective vertebra.

* * * * *